(12) United States Patent
Boyer et al.

(10) Patent No.: US 6,202,923 B1
(45) Date of Patent: Mar. 20, 2001

(54) AUTOMATED PHARMACY

(75) Inventors: Joseph H. Boyer; James P. Boyer, both of Johnson City; William S. Bennett, Binghamton, all of NY (US)

(73) Assignee: Innovation Associates, Inc., Johnson City, NY (US)

( * ) Notice: Subject to any disclaimer, the term of this patent is extended or adjusted under 35 U.S.C. 154(b) by 0 days.

(21) Appl. No.: 09/379,891

(22) Filed: Aug. 23, 1999

(51) Int. Cl.[7] .................................................... G06F 17/00
(52) U.S. Cl. ............................................. 235/375; 235/383
(58) Field of Search .................................... 235/375, 383, 235/385; 364/479.01–479.02, 479.06–479.07, 479.11–479.14, 478.07–478.08, 478.01; 221/75, 7, 2, 13, 200, 258; 53/53–55

(56) References Cited

U.S. PATENT DOCUMENTS

| | | |
|---|---|---|
| 5,502,944 | 4/1996 | Kraft et al. . |
| 5,597,995 | 1/1997 | Williams et al. . |
| 5,660,305 | 8/1997 | Lasher et al. . |
| 5,700,998 | 12/1997 | Palti . |
| 5,713,485 | 2/1998 | Liff et al. . |
| 5,907,493 | * 5/1999 | Boyer et al. . |

FOREIGN PATENT DOCUMENTS

WO 98/09598  *  3/1998  (WO) .

* cited by examiner

*Primary Examiner*—Thien M. Le
(74) *Attorney, Agent, or Firm*—Salzman & Levy

(57) ABSTRACT

A method and an automated pharmacy system to alleviate the risk posed by a queue of printed labels for prescription vials that occurs at the printer. The method and system eliminate the need for physically transferring paperwork from one site (the imaging station) to another site (the filling station). Elimination of the physical transferring step smooths the flow of the dispensing operation, and hence, improves the throughput of the automated pharmacy, and further, helps to prevent the association of the wrong paperwork with a given prescription.

57 Claims, 8 Drawing Sheets

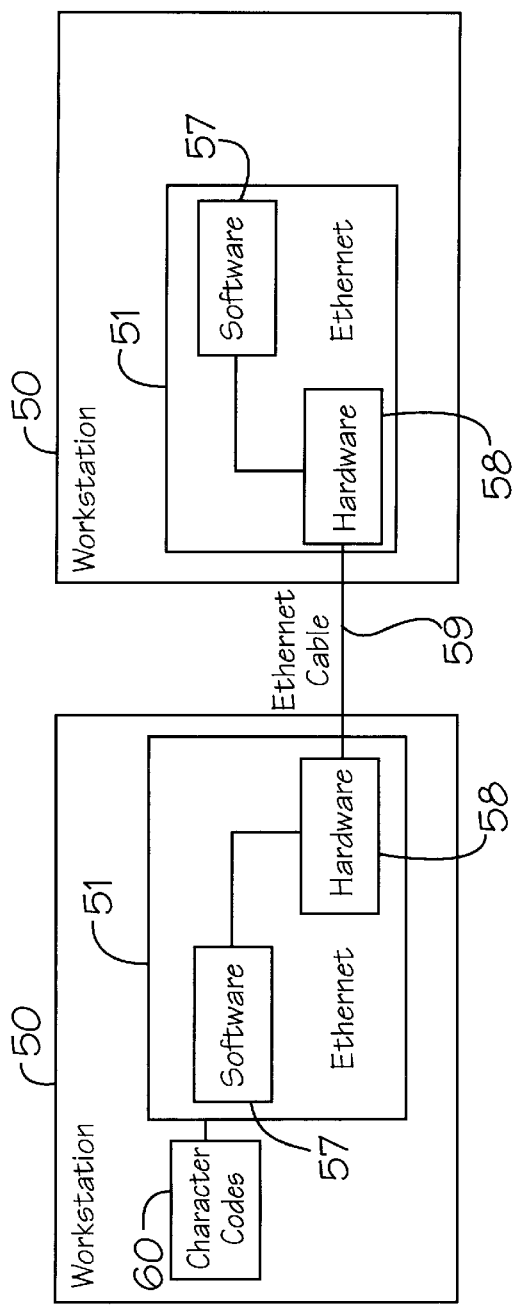
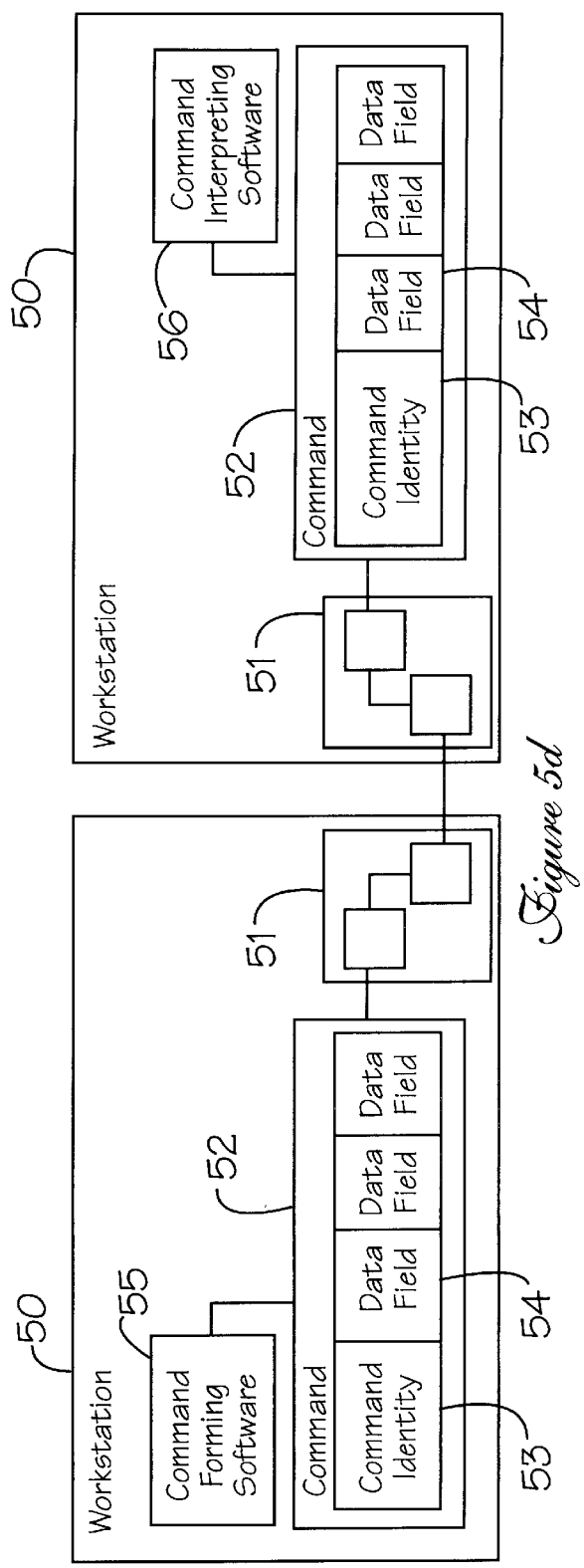
Figure 5c
Figure 5d

AUTOMATED PHARMACY

RELATED PATENT APPLICATION

1. Field of the Invention

The present invention relates to automated pharmacies and, more particularly, to an automated pharmacy that is more accurate and has a prescription filling throughput greater than those of other systems.

2. Background of the Invention

In a typical prescription filling system illustrated in U.S. Pat. No. 5,597,995, for AUTOMATED MEDICAL PRESCRIPTION FULFILLMENT SYSTEM HAVING WORKSTATIONS FOR IMAGING, FILLING, AND CHECKING THE DISPENSED DRUG PRODUCT, issued to WILLIAMS et al., a written prescription is presented to a pharmacy and read by a pharmacist or clerk. The pharmacist or clerk at the pharmacy also inquires about the malady of the patient directly, and elicits any additional information from him or her. This information, along with the prescription, is then entered into a computer called a "host" computer via a computer keyboard, and is stored in a database. The computer creates a prescription number associated with the entered data and stores it with the data in the database. The host computer then sends this data record to a first computer, also within the imaging station. The first computer then sends all of this information separately to a first printer, which prints a vial label having a barcode, and to a second printer which then prints a label containing a prescription number, which is affixed to the paper prescription received from the patient. Thereafter, the paper prescription is placed in a scanner, producing a computerized image that is stored in a database. The image is associated in the database with the prescription number. Thereafter, the first computer sends the data to a second computer associated with a filling station, where it is placed in that second computer's database.

In practice, the first printer typically also prints what is commonly referred to in the industry as a "prescription label," often a single sheet of adhesive-backed paper. It typically consists of a prescription vial label, patient "monograph" (explanations and instructions for the patient), a receipt, a duplicate receipt, and various auxiliary labels such as special warnings, bag labels, and the like. The resultant queue of labeled vials with these associated prescription labels causes confusion, lost time, and is a source of errors which may occur during the filling process.

The label is affixed to an empty vial at the first printer resulting in a labeled vial. At this time the labeled vial (and, in practice, associated prescription paperwork) are sent to the filling station. At the filling station, the second computer, which has received the prescription data record from the first computer, controls a drug dispenser. A barcode scanner is used to read the barcode on the label of the vial, sending the prescription number encoded thereon to the second computer. The second computer then searches its database for the prescription number read from the barcode on the vial label. When it is found, the second computer uses the data to dispense the correct type and number of tablets from the automated dispensing system or a manual filling process, into the vial. With the WILLIAMS et al. system, the vial label is produced in the printer, which results in a queue of labeled vials and paperwork, along the system path, between the imaging workstation prescription label printer and the prescription filling station where both automated and manual filling can take place. Unfortunately, this creates potential for confusion and error.

The present invention, on the other hand, represents a method and a system to alleviate the risk of errors in filling posed by the queue of multiple labeled vials and their associated paperwork that exists at the filling station. The present invention does so by allowing a workflow in which only one unfilled labeled vial and its associated prescription label paperwork exist at the filling station at any one time. In the event that the pharmacy handles very high volume, and more than one filling station is employed, still only one unfilled labeled vial and its associated prescription label paperwork will exist at each separate filling station.

Additionally, the present invention eliminates the need to physically transfer the labeled vial and prescription paperwork from one site (the data entry workstation) to another site (the filling station). Elimination of the physical transferring step smooths the flow of the dispensing operation, and hence, improves the automated pharmacy's throughput.

The WILLIAMS et al. system also has an additional problem, when attempting to give high priority (the order in which vials are filled) to a particular prescription at the filling station. Filling prescriptions out of the originally intended order increases the likelihood of providing the wrong paperwork with any particular vial, because it requires the operator to search through the queue of labeled vials and prescription label paperwork.

The present invention, by removing the physical transfer of paperwork and the queue of labeled vials and paperwork at the filling station, greatly reduces the probability of mistakes when a particular prescription is taken out of its normal position in the queue.

In the present invention, as in the prior art, a prescription number is generated within the computer at the data entry workstation and associated with the entered data record. The image of the paper prescription is scanned in. At this point the various patient information and patient history already in the database can be updated, as can all of the new information about the present prescription associated with it. Then the data and the prescription number are sent to the second computer, located at the filling station, which controls a second printer that prints a label containing the barcode of the prescription number. The label is affixed to a vial, again resulting in a labeled vial. The barcode is read by a scanner connected to the second computer. The second computer or the first computer then searches the database for the prescription number read from the barcode on the vial. When this prescription number is found, the accompanying data block is sent to the second computer, which uses the data to dispense the correct type and number of tablets from the dispenser into the vial.

Both the WILLIAMS et al. and the inventive systems include a checking station, having its own computer or terminal, at which a pharmacist checks the filled vial against the data and the image of the prescription displayed on a screen. The tablets in the vial are also compared with a stored picture of the type of tablet which has been dispensed for this prescription. This validates that the correct drug has been dispensed.

Using the system of this invention as compared to the WILLIAMS et al. system, however, it is unnecessary to have a potentially confusing queue of labels between the first computer and the filling station. This improves reliability of the operation and substantially reduces errors. In addition, since there is no flow of labels or vials from the data entry workstation (the imaging workstation in the WILLIAMS et al. system) to the filling station which must be manually tracked, the efficiency and throughput of the pharmacy is improved.

In the event that a particular prescription requires a fill-next priority, as for example when a patient arrives at the pharmacy and chooses to wait for the medication, the system of this invention makes it easier to accomplish this task without errors, as only the one unfilled labeled vial exists at the filling station (or at any one filling station) at any one time. This results in streamlining the flow of prescription data, so that the data is held in the computers until needed. In other words, the data is not floating about the pharmacy, as is likely in the WILLIAMS et al. system.

Furthermore, in the WILLIAMS et al. system, it is possible for the operator to scan the wrong vial label at the filling station, and thus, the wrong data could be associated with the intended prescription, because a number of labels were in existence at the same time. The present invention prevents this, however, by scanning the barcode on the label of the vial into which the medicine is to be dispensed, since it is the only unfilled labeled vial at the filling station.

In U.S. Pat. No. 5,713,485, issued to LIFF et al. on Feb. 3, 1998, entitled DRUG DISPENSING SYSTEM, an automated drug dispensing system is shown. The system comprises a plurality of prepackaged pharmaceuticals. The varieties of pharmaceuticals are each associated with a code. A controller receives requests and generates dispensing signals that cause a dispenser to dispense the packaged pharmaceuticals. After dispensing the pharmaceutical, its code is checked against that originally requested.

In U.S. Pat. No. 5,700,998, issued to PALTI on Dec. 23, 1997, for DRUG CODING AND DELIVERY SYSTEM, a drug dispensing system having coded tablets or pills is illustrated. The code is placed directly on the tablet and then compared to the code associated with the requested pharmaceutical, which is meant to ensure that only the exactly ordered pharmaceutical is dispensed.

In U.S. Pat. No. 5,660,305, issued to LASHER et al. on Aug. 26, 1997, entitled AUTOMATIC PRESCRIPTION DISPENSING SYSTEM, a dispensing system having a multiplicity of pill dispensers is shown. The dispensers are arranged in rows and columns. Empty pill bottles are conveyed past the dispensers. Pills are released into the individual bottles as they pass under the proper dispenser, thus allowing for simultaneous dispensing. The correct number of pills is counted prior to dispensing, wherein the pills are released en masse.

In U.S. Pat. No. 5,502,944, issued to KRAFT et al. on Apr. 2, 1996, for MEDICATION DISPENSER SYSTEM, a dispenser is shown that contains a number of containers for holding a select quantity of medications. A packaging apparatus under robotic control dispenses the prescription from the containers to a package, thus preventing cross-contamination.

SUMMARY OF THE INVENTION

In accordance with the present invention, there is provided a system for operating a pharmacy. The system provides a greater throughput than previous systems by virtue of eliminating a paper trail and a queuing of prescription labels, in which vials and labels are transported in piles. As one of the first steps, a prescription number is assigned to the written or communicated prescription request. This prescription number is then combined with data transmitted from a first location or operating station, usually comprising a computer. The prescription number is associated with the prescription and this data.

Then, the data and the prescription number are sent to a second location or operating station, usually comprising a second computer. The second computer controls a second printer that prints a label containing the barcode and the prescription number. The label is affixed to a vial, resulting in a labeled vial. The barcode is read by a scanner connected to the second computer. The second computer or the first computer then searches a database for the prescription number read from the barcode on the vial. When this is found, the accompanying data block is used by the second computer to dispense the correct type and number of tablets from the dispenser into the vial.

The system comprises a checking station, having its own (third) computer or terminal, at which a pharmacist checks the filled vial against the data and the image of the prescription displayed on a screen. The tablets in the vial are also compared with a stored picture of the type of tablet which has been dispensed for this prescription. This validates that the correct drug has been dispensed.

It is an object of this invention to provide an improved pharmaceutical dispensing system.

It is another object of the invention to provide an automated medication dispensing system having improved throughput.

It is a further object of this invention to provide a pharmaceutical dispensing system that is not subject to errors in the dispensing of medications.

It is still another object of this invention to provide an automated pharmaceutical dispensing system that can be used in pharmacies of any size.

It is a further object of this invention to provide a pharmaceutical dispensing system in which the workflow may be configured as needed in any pharmacy.

BRIEF DESCRIPTION OF THE DRAWINGS

A complete understanding of the present invention may be obtained by reference to the accompanying drawings, when considered in conjunction with the subsequent detailed description, in which:

FIGS. 5a–5d illustrate the communication amongst workstations;

For purposes of brevity and clarity, like elements and components in the figures will bear the same designations and numbering throughout.

DESCRIPTION OF THE PREFERRED EMBODIMENT

Generally speaking, this invention features a system for improving the workflow of medication dispensing, and for assuring freedom from errors during the filling of prescriptions at an automated pharmacy. The novel system further pertains to a pharmacy computer network that allows an operator at one workstation to access data from any other workstation. A data bus connects a filling workstation with a microprocessor which controls a particular dispenser. This data bus prevents messages moving between the filling workstation and the microprocessors from interfering with information flow among all other workstations.

Figure 1:
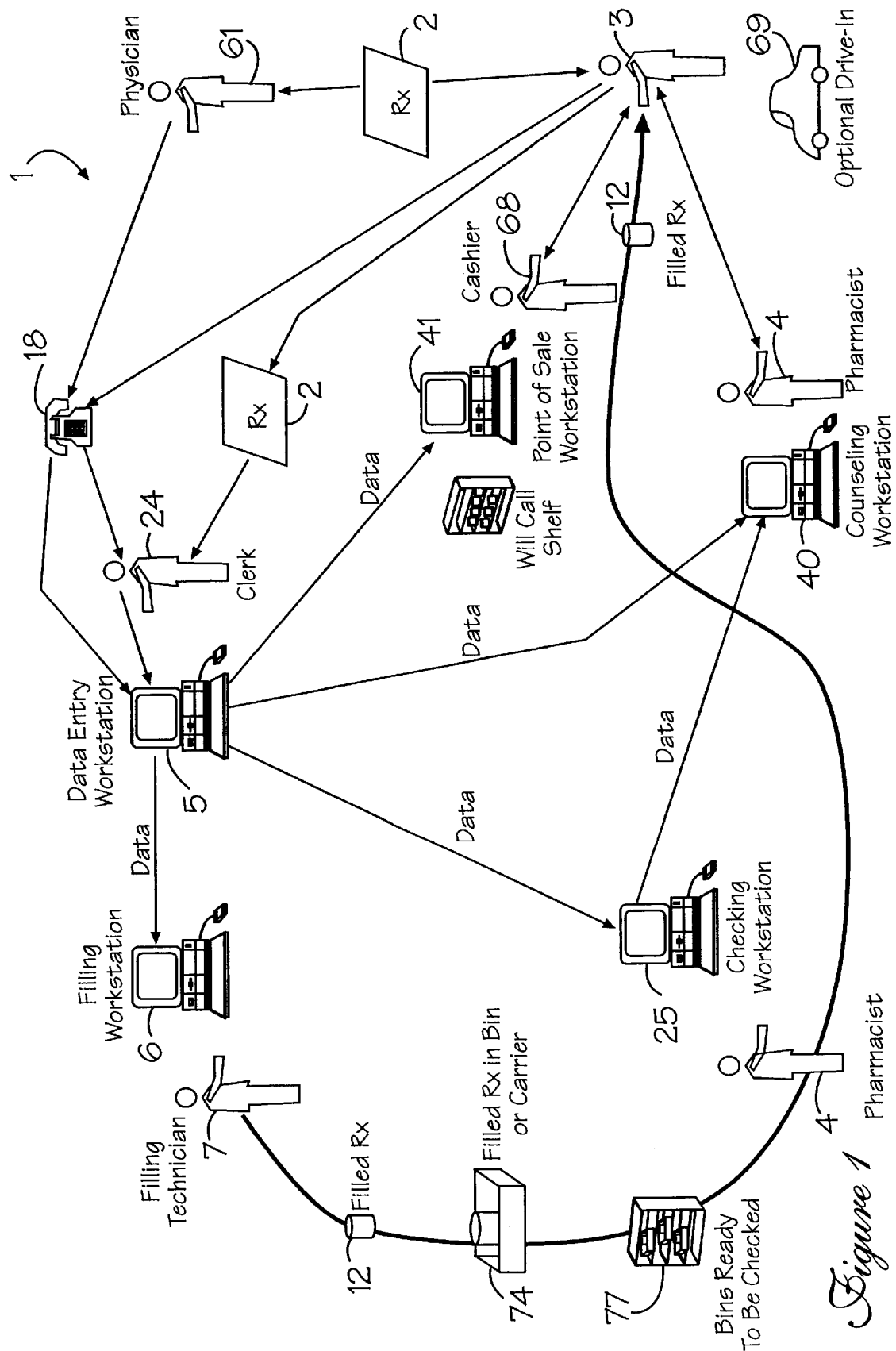
FIG. 1 illustrates a schematic view of the medication dispensing system in accordance with the present invention.

Referring now to FIG. 1, what is shown is a medication dispensing system 1 comprising a data entry workstation 5, a filling workstation 6, a checking workstation 25, a counseling workstation 40 and a point-of-sale (POS) workstation 41. While it is preferred to include all five above-identified workstations, the medication dispensing system 1 is adapted to have fewer or more workstations. Moreover, the functions of several workstations may be combined. However, data entry, filling and checking are the three basic sub-systems which must be included in any configuration of medication dispensing system 1. To obtain a better understanding of system 1 as a whole its individual workstations 5, 6, 25, 40 and 41 are explained hereinbelow.

The data entry workstation 5 contains data entry software and is typically part of the pharmacy management system software, which most pharmacies use at present. The technique by which the pharmacy management software is made available to the data entry workstation may be through the use of a screen window within which an interface to the pharmacy management software is presented, or alternatively, through the use of an electrical switching device (not shown) that switches the computer display, keyboard and mouse to the pharmacy management system computer to or from the workstation.

Figure 3:
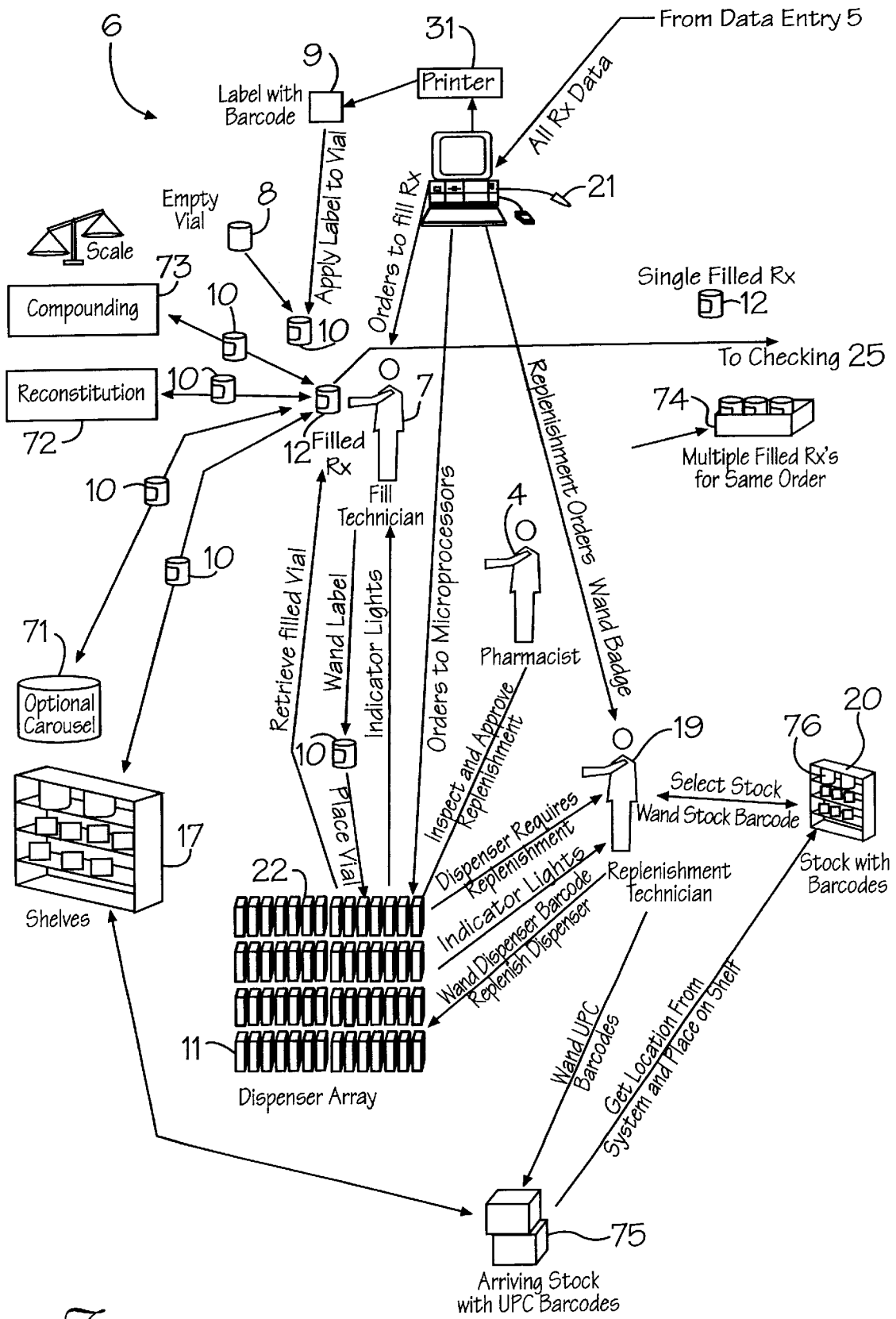
FIG. 3 shows a schematic view of the filling workstation in accordance with the present invention.

The filling workstation 6 contains software to control automated dispensers 22 (FIG. 3) and to direct a fill technician 7 in the filling of prescriptions both from the automated dispensers 22 (FIG. 3) and from shelves 17 and 20 (FIG. 3). Shelves 20 are specifically used to replenish the dispensers 22.

The checking workstation 25 presents a pharmacist with the prescription data, a scanned image of the paper prescription, if present, and an image of the tablet or capsule to be dispensed. This enables the pharmacist to check and approve the prescription. A pharmacist is able to check the filled prescription for accuracy and verify that the label is also accurate and complete and that the drug utilization review has been completed.

The counseling workstation 40 provides the pharmacist with information on the patient 3, any other medications the patient 3 is currently taking, and information relating to the medication being dispensed. Moreover, the counseling workstation 40 assists the pharmacist in advising the patient 3 on the use of the medication and on other health issues.

The point-of-sale (POS) workstation 41, in most instances merely a cash register, is where a patient's payment is accepted by a clerk or cashier. Point-of-sale workstation 41 may include a barcode reader 41a (FIG. 8) to identify the prescriptions for which payment is being made, and a signature pad 41b (FIG. 8) to record an image of the patient's signature, when required. Point-of-sale workstation 41 may also be used to trace the status and location of a prescription in the workflow through the pharmacy.

In the pharmacy, there is a pharmacist 4, a data entry technician 24, a fill technician 7, a cashier/clerk 68 and a replenishment technician 19 (FIG. 3). If necessary, pharmacist 4 can assume the duties of any of the others. Fill technician 7, cashier/clerk 68, and replenishment technician 19 (FIG. 3) may assume some or all of the responsibilities of each other. It is preferred to have separate individuals for these tasks, but it is also possible that only one individual may perform all tasks. Conversely, if several computers are disposed at one workstation 5, 6, 25, 40 or 41, more than one individual may perform the same task. In operation, a physician 61 creates a prescription 2 for a patient 3. Prescription 2 is given to patient 3 for personal delivery to data entry technician 24. The data entry technician may also be provided with prescription 2 directly by physician 61 or qualified person in the physician's office staff (not shown) via telephone 18, fax, or other method. In the case of refills, the patient 3 may simply place an order without appearing in person.

Patient 3 presents prescription 2 either within the pharmacy or at a drive-in window 69. In the case of refills, the patient may communicate with a computer in the pharmacy by telephone, providing the information about the desired refill through the use of the touch-tone keyboard in response to synthesized voice requests by the computer, often called Interactive Voice Response ("IVR").

Figure 2:
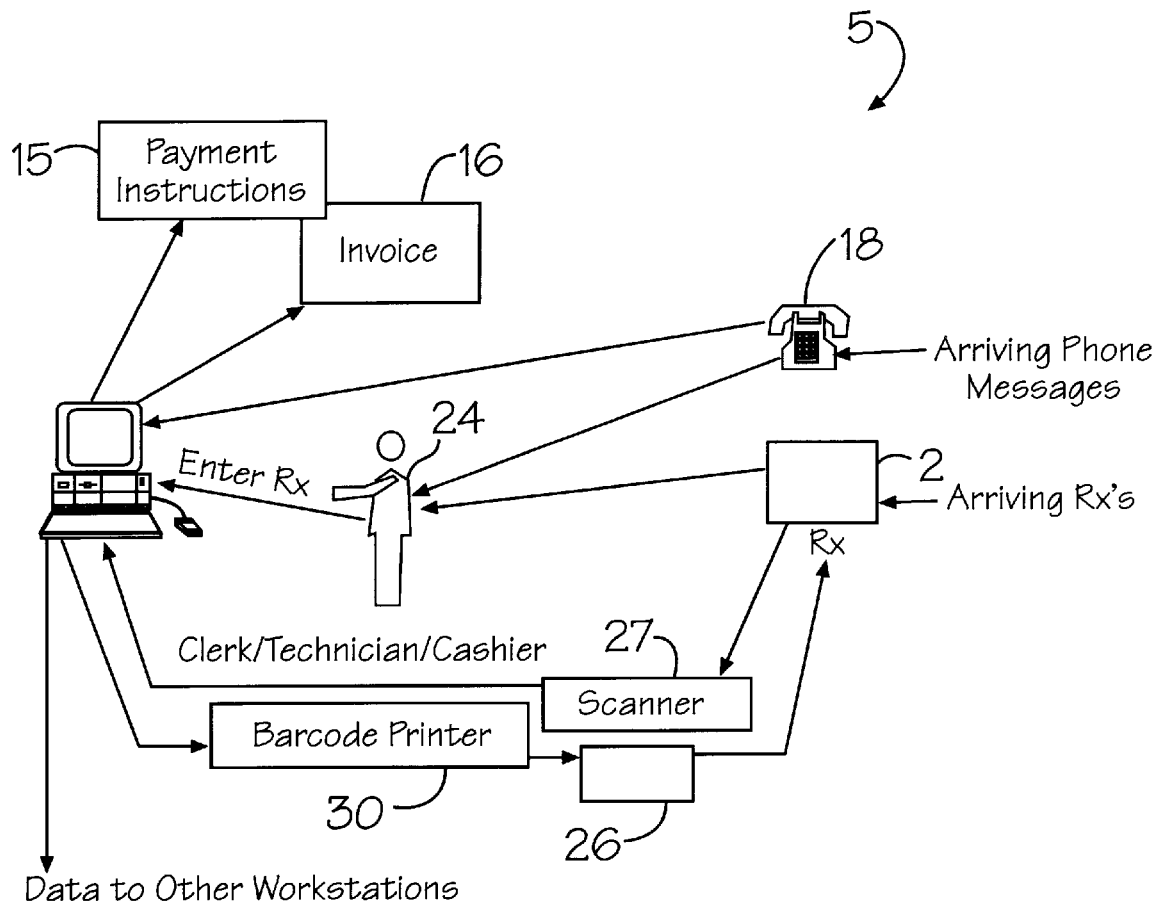
FIG. 2 depicts a schematic view of the data entry workstation in accordance with the present invention.

Referring now to FIG. 2, shown is the data entry workstation 5. Upon receiving refill information via telephone 18 or physical prescription 2, data entry technician 24 enters the data into data entry workstation 5. The information received from prescription 2 and from the patient 3 contains, at a minimum, the patient's name, the patient's address, the physician's name, the type of drug, the dosage size of the drug, the quantity of drug, the date prescribed, physician's instructions to the patient, the number of refills allowed, and whether the substitution of a generic version of the drug is permitted by the physician.

In a typical pharmacy management system 81 (FIG. 6) in accordance with this invention, data entry technician 24 is asked to consult patient 3 to determine method of payment, through a prescription insurance service with patient copayment, for example. Data entry technician 24 then enters this information into data entry workstation 5.

Similarly, adjudication is also handled by the pharmacy management software 81 at this point. Adjudication is determining whether the insurance company or HMO will allow the patient to use this drug or whether another drug must be substituted. Yet another function of the pharmacy management software 81 is drug utilization review. This requires a pharmacist to examine computerized records of the patient's illnesses and other medications to detect possible incompatibilities.

Data entry workstation 5 creates a new data record or consults and updates an existing data record. Data entry workstation 5 transmits all information via a database to filling workstation 6 and checking workstation 25. The information includes a recognized code indicating the type of drug and the dosage size, the number of tablets to be dispensed, a prescription number assigned by data entry workstation 5, the patient's name and address, the physician's name, physician's instructions to the patient, date of the prescription, number of refills allowed, whether a generic version of the drug has been used, and possibly other information.

Barcode printer 30 at data entry workstation 5 prints a barcode label 26 representing the assigned prescription number for prescription 2. Barcode label 26 also contains a printed prescription number which is the same one encoded in the barcode itself. Barcode label 26 may optionally contain other information from the prescription data record. Barcode label 26 is then affixed to either the front side or the back side of prescription 2. It should be understood, however, that a barcode can be printed directly on the prescription 2. A scanner 27, which may be located anywhere in the pharmacy, scans prescription 2 and produces a digitized image. Alternatively, instead of scanner 27, a digital camera (not shown) may be used. In either case, this step may be preceded by a wanding of the barcode affixed to prescription 2. The image is stored for later use in checking the prescription 2 and as part of the pharmacy archives. At any time, a list of the prescriptions to be filled may be viewed on the screen of the data entry workstation or any of the other workstations; the particular order in which they are to be filled may be noted; and the filling order of any particular prescription may be changed.

Referring now to FIG. 3, the workings of the filling workstation 6 are illustrated. The filling process is performed by a fill technician 7, when possible, or by a pharmacist 4 if necessary. Filling may be performed manually or automatically (i.e., machine-assisted).

In manual filling, printer 31 is located at filling workstation 6 and utilizes the transmitted information from data entry workstation 5 to print a label 9, which is affixed to the empty medication vial 8, container or package, not shown. This results in a labeled vial 10. Now, the labeled vial 10 is ready to be filled with the proper medication, not shown.

Manual filling includes counting pills, tablets or capsules by hand, retrieval of packages (i.e., units of use or stock-keeping units) from shelves 17 or motorized carousel shelving 71, the reconstitution 72 of certain medications, and compounding 73. Reconstitution is adding sterile water to powders, while compounding 73 is mixing medications immediately prior to dispensing to the patient. Solid medication is placed in labeled vial 10. Other medication (e.g., liquid, gels) may remain in a package to which label 9 is attached. The filled vial 12 or packages (not shown) are then forwarded to the checking workstation 25 (FIG. 4), either singly or combined in pans or bins 74, where several medications are intended for the same order. Color coding of each bin 74 can be used to indicate priority of completion.

The various operations performed at the filling workstation 6 are directed by the computer system, which provides information as to where the medication is found on the shelves 17 or 71. Shelves 17 and 71 can contain or store certain items that cannot be conveniently dispensed automatically (e.g., creams in a tube). One advantage of this information management system is that frequently-requested medications can be placed on the shelves nearest the filling workstation. Thus, the overall time spent in retrieving medications is reduced.

Automatic filling utilizes an array 11 of automatic tablet or capsule dispensers 22. Using transmitted information from data entry workstation 5, printer 31 prints a vial label 9 to be affixed to empty vial 8. Included on this label is a barcode representing the assigned prescription number.

Based on the information received from the data entry workstation 5, including the drug type (pills, tablet or capsule), number, and dosage size required by prescription 2, filling workstation 6 selects a dispenser 22 in automatic dispenser array 11. A code is sent to dispenser 22 ordering the specific number of tablets required by prescription 2 be counted and held in a buffer compartment.

At approximately the same time, the fill technician 7 receives an order on the screen of filling workstation 6 which indicates to technician 7 that this particular prescription 2 will be dispensed by automatic dispenser array 11. Filling workstation 6 displays instructions to select a certain size vial, which technician 7 uses to select empty vial 8. Technician 7 affixes label 9 to vial 8, thereby creating a labeled vial 10. Printer 31 does not print label 9 until the specified prescription 2, associated therewith, is displayed on filling workstation 6. This prevents any possibility of label 9 being incorrectly affixed to the wrong vial 8.

Next, technician 7 uses a wand 21, connected to filling workstation 6, to scan the barcode on label 9. Upon receipt of the barcoded information, which represents the prescription number of prescription 2, filling workstation 6 then instructs dispenser 22 to display a ready light. Fill technician 7 places vial 10 underneath the buffer compartment of dispenser 22. When the dispenser 22 detects that vial 10 is in position, it releases the tablets from its buffer compartment into labeled vial 10, thus producing filled prescription 12.

Again, the filled vials 12 are forwarded to the checking workstation 25, either singly or combined in pans or bins 74, which may be barcode identified. Color coding may be applied to the vials to indicate to the pharmacist at the checking station 25 that a particular prescription or set of prescriptions in the bin is to be checked ahead of other prescriptions. Once the pans or bins 74 contain a completed group of prescriptions in one order, they may be stored in a holding area 77 (FIG. 1) prior to being checked and distributed by pharmacist 4.

Figure 4:
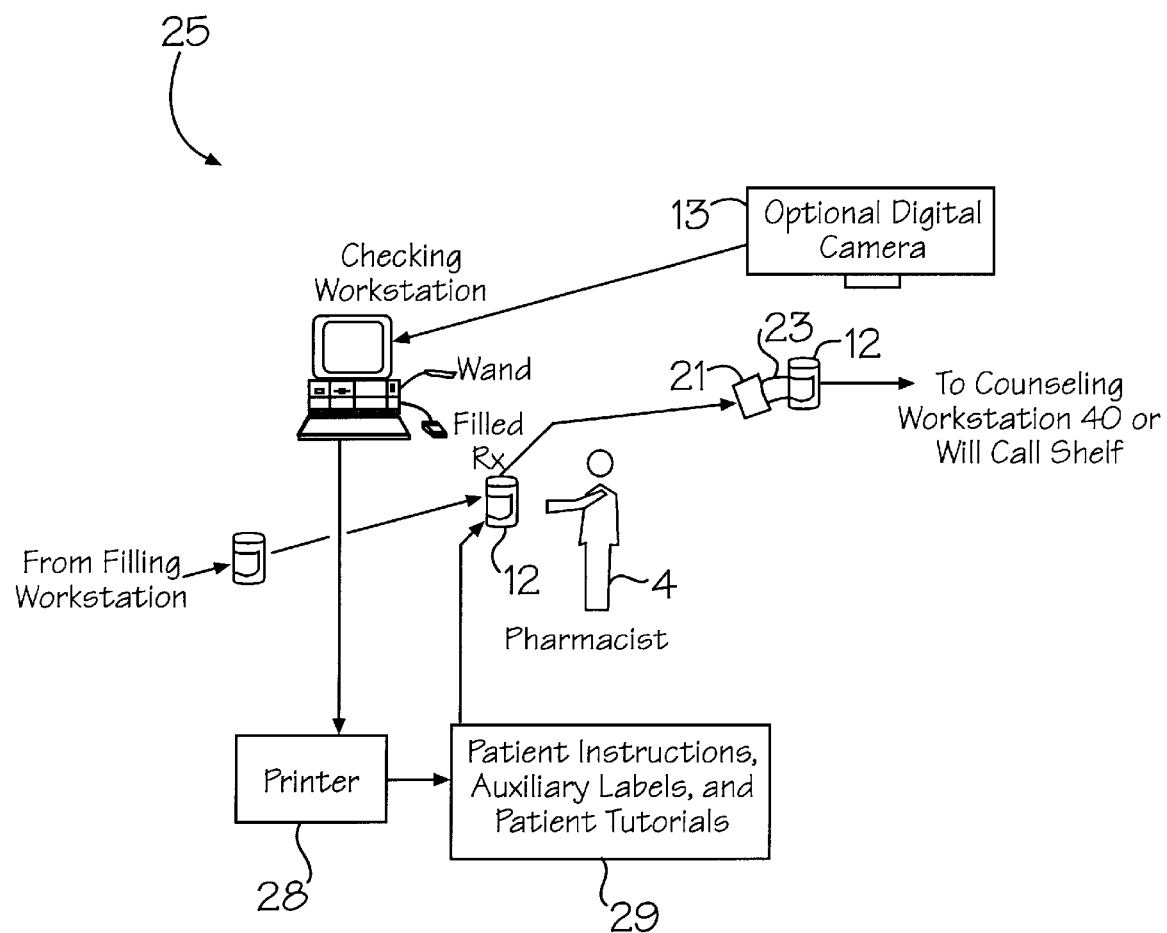
FIG. 4 is a schematic view of the checking workstation in accordance with the present invention.
Figure 5A:
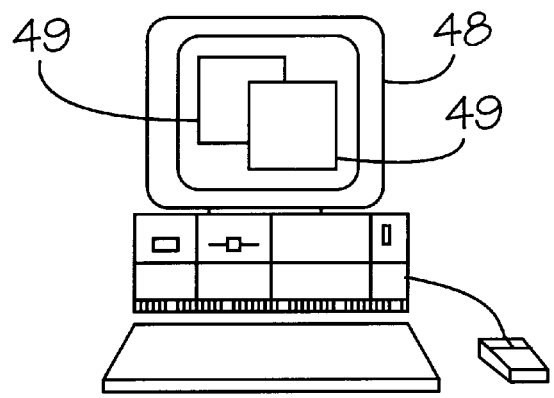
Figure 5B:
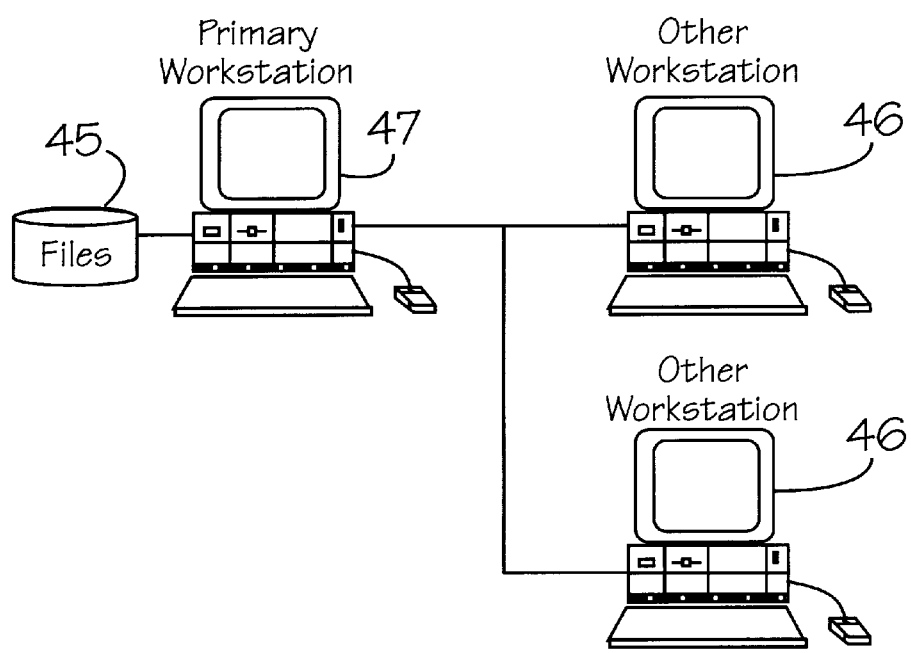

Referring now to FIG. 4, shown is a checking workstation 25 at which pharmacist 4 checks the filled prescription order. Pharmacist 4 may, at this workstation, view a list of prescriptions in process, and note which prescriptions are ready to be checked. Pharmacist 4 may also note which prescriptions that are ready to be checked should be accompanied by other prescriptions not yet filled (for example, if those prescriptions are for the same patient), and may adjust the filling priority of such prescriptions. Pharmacist 4 then begins the checking process. The pharmacist 4 first scans or wands the barcode associated with a prescription number on the filled vial 12 or package, not shown. In lieu of scanning the barcode, the pharmacist may elect to enter the prescription number manually. The checking workstation 25 uses the prescription number to obtain information from the database. The checking workstation 25 associates the image (not shown) of the drug with the information it receives from the database. This image appears on a computer screen at checking workstation 25. The pharmacist examines the image and compares it with the tablet or capsule or package, in the case of units of use to assure that the medication is, in fact, correct. Also, the label is inspected, comparing its information to the information provided at the checking workstation 25. The image of the paper prescription may also be compared at that time. Pharmacist 4 verifies that the drug utilization review has been performed. If all information is correct and the medication is the correct type, strength, and amount, pharmacist 4 approves the prescription.

Optionally, at checking workstation 25, pharmacist 4 can position an uncapped, filled prescription 12 under a digital camera 13. The label 9 faces a pair of mirrors (i.e., curved mirror 23 and plane mirror 21). Digital camera 13 takes a picture of the capsules inside filled prescription 12 and, on the same image, an image of label 9 transmitted by mirrors 21 and 23. Mirror 23 is curved so that it reflects a flattened, straight image of the label 9 into mirror 21. Because the image of label 9 is unavoidably reversed by mirror 23, mirror 21 is used to reverse the image of label 9 again so that it is readable. Alternatively, this reversal may be accomplished through computer software in the workstation. The combined picture of the tablets within filled prescription 12 and the label 9 is then transmitted to checking workstation 25, where it is combined with the other information about prescription 2 to form a permanent record thereof.

It can thus be seen that the image with the prescription number in the database can be accomplished by two means:
  a) by scanning the paper prescriptions in a strict sequence so that each one is scanned immediately after the prescription number is assigned, so that, if the sequence is violated, then the wrong paper prescription image will become associated with a given prescription number; and
  b) by printing out a barcode label and attaching it to the paper prescription, which again must be done in strict sequence. However, then the scanning of the paper prescription can be deferred, and the correct association effected by scanning the barcode pasted to the paper prescription at the time the paper prescription is scanned.

Figure 7:
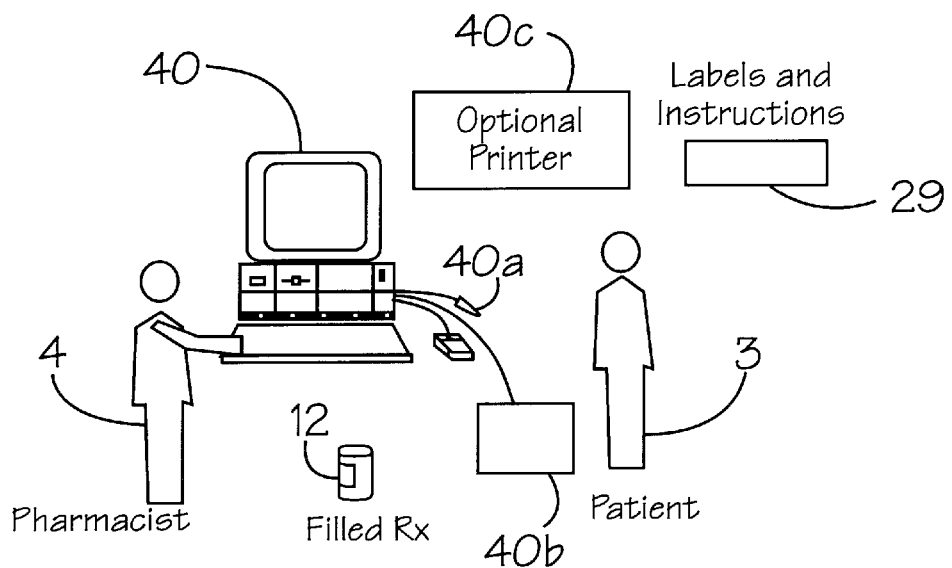
FIG. 7 represents a patient and pharmacist at a counselling workstation.

Furthermore, pharmacist 4 can provide counseling to patient 3 at checking workstation 25 or at a separate counseling workstation 40, as shown in FIG. 7. In either case, a printer 28 or printer 40c prints out patient information and/or patient tutorials 29 on the drug of prescription 2, and various auxiliary labels 29 (some of which may be preprinted) which the pharmacist 4 affixes properly. Alternatively, this information may be been printed out previously at the filling or checking workstation. Printer 28 or printer 40c may also print out tutorial material to be given to the patient, the material containing general instructions on self-care of his or her illness. Pharmacist 4 provides the medication, patient instructions, and certain other items (e.g., a bag/receipt label) to the cashier at the point-of-sale workstation 41.

Figure 8:
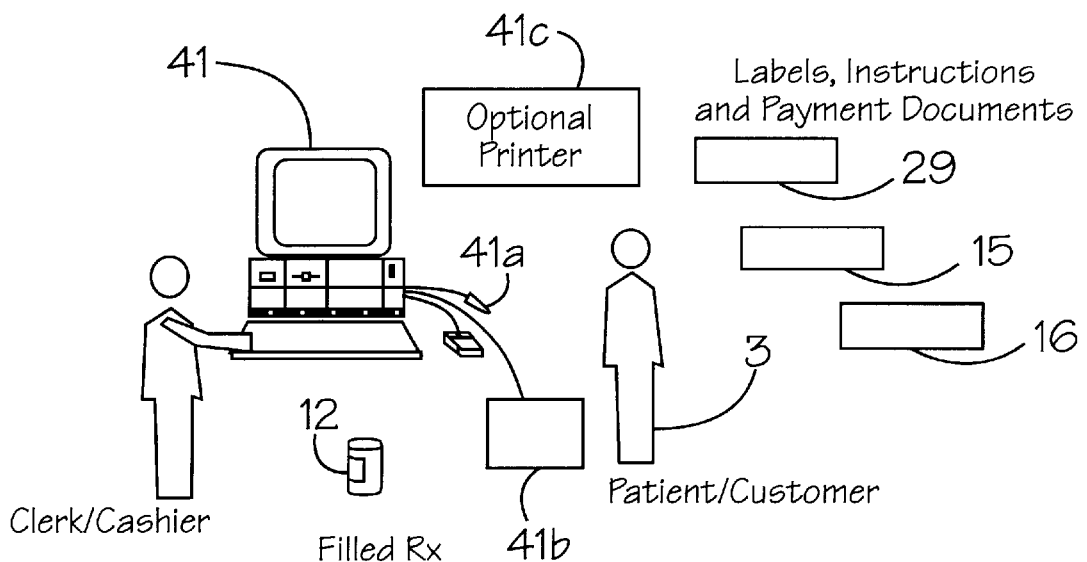
FIG. 8 represents a customer and clerk/cashier at a point-of-sale workstation.

Referring again to FIGS. 1 and 2 and also FIG. 8, if payment instructions 15 and invoice 16 have not already been printed out at another workstation, workstation 41 prints payment instructions 15 and invoice 16 for prescription 2, which the data entry technician 24 or clerk/cashier 68 may use to accept payment from patient 3.

Referring again to FIG. 3, after a period of time, certain dispensers in dispenser array 11, say, a dispenser 22, become empty or too low for filling a prescription. At this point, filling workstation 6 will indicate to an operator that a particular dispenser 22 is empty or low on medication. Filling workstation 6 provides information on its screen to replenishment technician 19 to refill dispenser 22 with a certain type and size of tablet or capsule. Technician 19 selects a supply container 76 for the correct drug and size from stock 20. On the supply container is a barcode indicating the drug type and size. Technician 19 wands the barcode, which informs filling workstation 6 of the drug type and size. If this is correct, filling workstation 6 then lights a replenish light (not shown) on dispenser 22. Technician 19 is then told to extend the drawer of dispenser 22 to the replenish position and, after that action is complete, to press a key on the keyboard of filling workstation 6. Filling workstation 6 sends a message to dispenser 22 to unlock its replenishment door (not shown). Technician 19 can now replenish dispenser 22.

However, filling workstation 6 does not immediately place dispenser 22 back into service. Pharmacist 4 may optionally physically inspect dispenser 22 to ensure that the correct tablets or capsules have been placed therein. Pharmacist 4 must then wand a badge he or she wears, indicating to filling workstation 6 that this is authorized pharmacist 4. Next, pharmacist 4 scans or wands dispenser 22, at which time the hopper door of dispenser 22 unlocks and springs open. Pharmacist 4 inspects the contents and closes the door, indicating to filling workstation 6 that he or she has inspected dispenser 22 and approves of the replenishment. Filling workstation 6 then places dispenser 22 back into service.

As time passes, certain shelf locations 17 at which medication bottles, or stock-keeping units used by the fill technician 7 when manually filling orders are kept may become depleted. Shelf locations 20 may also become depleted as a result of dispenser replenishment. Technician 19 must restock the shelves 17 and 20. As cartons 75 of medications come into the store, technician 19 scans or wands the UPC barcode on the arriving stock bottles (not shown). The filling workstation 6 then indicates to technician 19 where to place the bottles.

Referring now to FIGS. 5a, 5b, 5c, and 5d, the inter-workstation communication of this invention is disclosed. As mentioned above, any of the workstations may function as any of the others. The screen 48 of each workstation has separate operating system display windows 49 for each of the workstation types. Within each window 49 there can be a hierarchically lower window 49 that groups particular work functions. Normally, each workstation type (e.g., data entry, filling, checking, etc.) uses the window only of its own type. However, a given workstation 5, 6, 25, 40, 41 can bring up the window for a different type of workstation for performing the work of the other workstation. For example, an operator at the checking workstation 25 can bring up the window 49 for and perform the work of data entry workstation 5, provided that all necessary peripherals are available at workstation 25.

Communication between workstations 50 is effected in one of two ways: one is through data entered into or read from the database; a second is by direct message transmission, which is accomplished by sending or receiving a series of individual characters, represented by ASCII character codes. These characters make up a series of commands which convey meaning. The individual character codes 60 are transmitted between workstations using one of several well-known industry-standard character transmission protocols, such as Ethernet. These protocols utilize standard hardware 58 and software 57 which are commercially available.

The commands 52 are composed of a command identifier 53 (i.e., a character string identifying a command type) and a group of data fields 54, each having a meaning which may be unique to the particular command type, each composed of a number of characters which may vary from one field to the next.

When a workstation 46 receives a string of characters through the Ethernet line, its Command Interpreting Software 56 first checks the initial characters of the string, thus isolating the character string 53 that identifies the command. The software 56 then determines which subroutine corresponds to this identifier. It branches to that subroutine, which in turn takes actions pertinent to the command. The actions may include, for example: (a) unpacking the data fields 54 in the command using knowledge of the character lengths of each data field, (b) using the data to print a label or send a further command to a drug dispenser, or (c) forming up a return command to the other workstation 47 that holds requested data.

Similarly, if a workstation must use a command to send or to request data, it utilizes its Command Forming Software 62, thereby creating a command 52 by selecting and inserting a command identifier 53, and by computing or selecting data fields 54 and inserting them into the command 52. Command 52 is sent, character by character, to the transmission protocol system 51 for the actual transmission.

Figure 6:
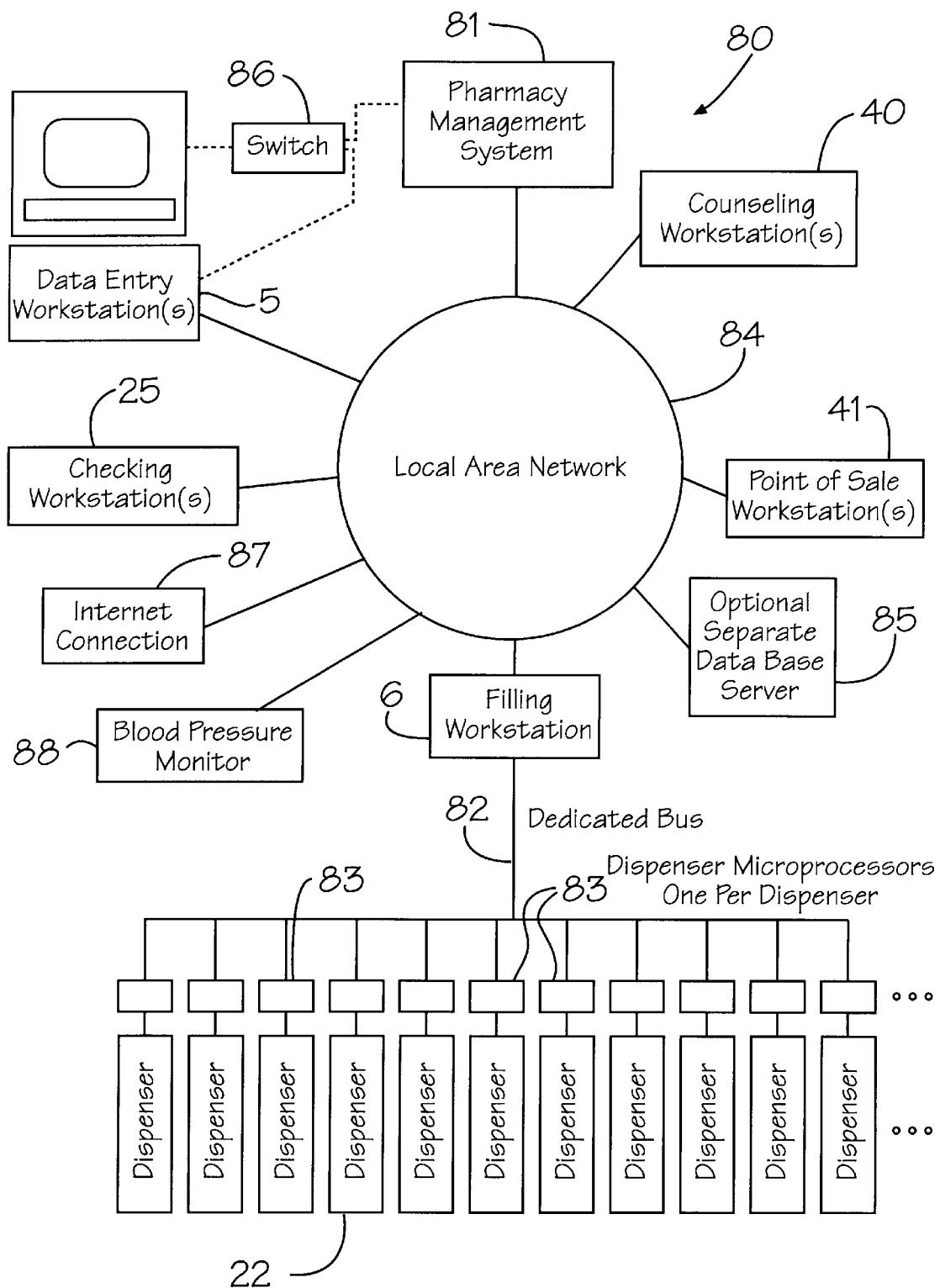
FIG. 6 is a block diagram depicting the arrangement of the computer network in accordance with the present invention.

Referring now to FIG. 6, illustrated is the configuration of a pharmacy computer network 80. In a retail pharmacy, a local area network 84 is provided, which is embodied as an Ethernet or other networking system known in the art. The hierarchical pharmacy computer network 80 consists of a local area network 84 connecting workstations 5, 6, 25, 40, 41 and, optionally, 81 and/or a separate database server 85. There may exist one or more of any workstation so as to allow for multiple operators.

The network comprises one or more of any workstation 5, 6, 25, 40, or 41. Each workstation may have, but should not be limited to, a personal computer or other device having: one or more microprocessors; a data entry mechanism, such as a computer keyboard, barcode scanner, voice recognition device, or touch screen; and a graphical display, with or without sound.

The optional, separate database server 85 may be added to the network, as aforementioned. The database may be contained in this server 85 instead of residing within one of the other workstations.

A separate pharmacy management system 81, which may optionally be connected via a separate long-distance network to a central pharmacy company computer complex, can also be either a part of a separate pharmacy network or be incorporated into the local area network 84. Alternatively, as mentioned above, the functions of the pharmacy management system can be incorporated into one of the workstations 5, 6, 25, 40, or 41.

If an operator at counseling workstation 40 needs information about a patient, the operator has access to the database. Similarly, when a patient 3 is retrieving a prescription, the cashier or other qualified operator at a point-of-sale (POS) workstation 41 can check the database to verify that the patient retrieving the prescription 2 is, in fact, receiving the proper prescription. The patient 3 himself or herself can also verify that the prescription has been filled properly either at the counseling workstation 40 or at an optional workstation (not shown) provided for that purpose.

An operator at any workstation 5, 6, 25, 40, 41 can access the database, barring any security protocols. Security protocols on certain computers prevent a cashier at the point-of-sale (POS) workstation 41 from accessing personal information about a patient. In other words, certain workstations might have access only to selected portions of the database. In this way, the filling workstation can be emulated at other workstations, so that filling can be controlled from, say, the data entry workstation should the pharmacist be alone in the store late at night. In this regard the system can allow optimum staffing of the pharmacy at different times of day.

A dedicated data bus 82 is located between filling workstation 6 and a plurality of microprocessors 83 controlling individual dispenser units 22. The bus 82 may also be an area network (not shown) similar to that of local area network 84.

Alternatively, pharmacy management system 81 may be directly connected to the display, keyboard and mouse of any of the workstations (reference numeral 5, for example) by providing an electrical switching device 86. Electrical switching device 86 connects the workstation computer (not shown) or the pharmacy management system computer (not shown) to the workstation display, keyboard and mouse.

Also optionally, local area network 84 can have an Internet connection 87 for allowing a pharmacist or patient to access information relating to the drug type/disease status, or patient self-care. The Internet connection can also be used to facilitate videoconferencing among professionals and schools, for example.

A blood pressure monitor 88 can also be connected to local area network 84 to permit data representative of a patient's blood pressure to be stored in the patient information database.

As stated above, one microprocessor 83 is provided for every dispenser 22. Instructions from the filling workstation 6 are passed to the microprocessors 83 via the data bus 82. Similarly, information can flow from the microprocessors 83 to the filling workstation 6 if, for example, the dispenser 22 malfunctions.

One filling workstation 6 can send and receive controlling messages (not shown) to a substantial number of microprocessors 83. It is preferred to have only one filling workstation 6; however, depending upon specific pharmacy requirements, the local area network 84 can include more than one filling workstation 6.

The fact that each dispenser 22 has its own microprocessor 83 enables a dispenser 22 to function with all shapes and sizes of pills, tablets and capsules without the use of different mechanical parts or adjustments. In other words, the microprocessor 83 allows the dispenser 22 to function with variations in medication size and shape. Various components (not shown) within the dispenser 22 are controlled through software programs, such as are disclosed, for example, in U.S. Pat. No. 5,671,262, for METHOD FOR COUNTING AND DISPENSING TABLETS, CAPSULES, AND PILLS, assigned to the common assignee, and hereby incorporated by reference. Internal parts of the dispenser 22 can be moved in any direction necessary to accommodate a pill of a particular size or shape.

The inventive configuration further prevents message traffic between filling workstation 6 and microprocessors 83 on the dedicated bus 83 from interfering with the flow of information among the workstations 5, 6, 25, 40, 41 and possibly 81 on the local area network 84.

Referring now to FIG. 7, there is shown a more detailed view of the counseling workstation 40, which comprises barcode reader 40a, signature pad 40b, and an optional printer 40c on which may be printed patient instructions, auxiliary labels and/or patient tutorials.

Referring now to FIG. 8, there is shown a more detailed view of the point-of-sale workstation 41, which comprises barcode reader 41a, signature pad 41b, and an optional printer 41c on which may be printed receipts, patient instructions, auxiliary labels and/or patient tutorials.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. Thus, for example, even when the system is applied in the absence of automated dispensing, it still provides automated control of the entire process.

Having thus described the invention, what is desired to be protected by Letters Patent is presented in the subsequently appended claims.

What is claimed is:

1. A system for operating a pharmacy, comprising:
   a data entry workstation for processing data relating to a prescription for medication, said data entry workstation having means for generating a prescription number associated with said prescription;
   means for introducing said prescription to said data entry workstation;
   a filling workstation operatively connected to said data entry workstation for dispensing a drug type into a container;

means disposed at said data entry workstation for sending said data and said prescription number to said filling workstation; and a printer, operatively connected to said filling workstation, for printing a label to be affixed to said container.

2. The system for operating a pharmacy in accordance with claim 1, further comprising:
   i) means for generating an original prescription image;
   ii) a display on which said original prescription appears; and
   iii) a checking workstation at which a pharmacist checks the filled container against said data and an image on said display of the appropriate drug type in order to validate that the correct prescription has been dispensed.

3. The system for operating a pharmacy in accordance with claim 2, further comprising means for preventing label printing until said prescription is ready to be filled at said filling workstation.

4. The system for operating a pharmacy in accordance with claim 3, wherein said checking workstation comprises a digital camera for transmitting an image of said container and its contents thereto for archival purposes.

5. The system for operating a pharmacy in accordance with claim 1, wherein said data entry workstation comprises means for generating a code representative of said prescription number.

6. The system for operating a pharmacy in accordance with claim 5, wherein said code comprises a barcode.

7. The system for operating a pharmacy in accordance with claim 1, wherein said container is a vial.

8. A system for operating a pharmacy, comprising:
   a data entry workstation for processing data relating to a prescription for medication, said data entry workstation having means for generating a prescription number associated with said prescription;
   means for introducing said prescription to said data entry workstation;
   a filling workstation operatively connected to said data entry workstation for dispensing a drug type into a container; and
   a printer, operatively connected to said filling workstation, for printing a label to be affixed to said container.

9. The system for operating a pharmacy in accordance with claim 8, further comprising:
   i) means for generating an original prescription image;
   ii) a display on which said original prescription appears; and
   iii) a checking workstation at which a pharmacist checks the filled container against said data and an image on said display of the appropriate drug type in order to validate that the correct prescription has been dispensed.

10. The system for operating a pharmacy in accordance with claim 8, wherein said data entry workstation comprises means for generating a code representative of a prescription number.

11. The system for operating a pharmacy in accordance with claim 8, further comprising a counseling workstation for providing information to a customer.

12. The system for operating a pharmacy in accordance with claim 8, further comprising a point-of-sale (POS) workstation for providing a filled prescription to a customer and for receiving payment therefor.

13. The system for operating a pharmacy in accordance with claim 10, wherein said code comprises a barcode.

14. The system for operating a pharmacy in accordance with claim 9, further comprising means for preventing label printing until said prescription is ready to be filled at said filling workstation.

15. A method of operating a pharmacy, comprising the steps of:
   a) associating a prescription number or a code representative thereof with a prescription;
   b) proximate a filling workstation, printing a label comprising said prescription number or said code representative thereof;
   c) affixing said printed label to a container; and
   d) using said prescription number or said code representative thereof to control dispensing of a drug type into said container.

16. The method in accordance with claim 15, wherein said dispensing control step (d) further comprises the step of:
   i) verifying that said information disposed on said label corresponds to said drug type to be dispensed.

17. The method in accordance with claim 15, further comprising the step of:
   e) verifying that the drug type disposed in said container is correct in accordance with said prescription number or said code representative thereof and in accordance with said original prescription.

18. The method in accordance with claim 17, wherein said label printing step (b) comprises printing additional information on said label and verifying the accuracy thereof.

19. The method in accordance with claim 17, wherein said verifying step (e) further comprises the step of:
   i) comparing said drug type in said container with an image of the correct drug type in accordance with said prescription number or said code representative thereof.

20. The method in accordance with claim 15, wherein said prescription number or said code representative thereof comprises a barcode.

21. The method in accordance with claim 16, wherein said dispensing control step (d) further comprises the step of:
   ii) using an algorithm to control dispensing means to dispense a proper quantity and size of drug type for filling said container.

22. A method of operating a pharmacy, comprising the steps of:
   a) associating a prescription number or a code representative thereof with a prescription;
   b) proximate a filling workstation, printing a label comprising said prescription number or said code representative thereof;
   c) affixing said printed label to a container; and
   d) using said prescription number or said code representative thereof as a control for dispensing a drug type into said container.

23. The method in accordance with claim 22, wherein said step (d) further comprises the step of:
   i) verifying that said information disposed on said label corresponds to said drug type to be dispensed.

24. The method in accordance with claim 22, further comprising the step of:
   e) verifying that the drug type disposed in said container is correct in accordance with said prescription number or said code representative thereof and in accordance with said original prescription.

25. The method in accordance with claim 24, wherein said label printing step (b) comprises printing additional information on said label and verifying the accuracy thereof.

26. A pharmacy management system for operating a pharmacy, comprising:
   a data entry workstation for processing data relating to a prescription for medication;
   means for introducing said prescription to said data entry workstation;
   a filling workstation at which a drug type is dispensed into a container; and
   a printer, operatively connected to said filling workstation, for printing a label to be affixed to said container.

27. The system for operating a pharmacy in accordance with claim 26, further comprising:
   i) means for generating an original prescription image;
   ii) a display on which an image of said original prescription appears; and
   iii) a checking workstation at which a pharmacist checks the filled container against said data in order to validate that the correct prescription has been dispensed.

28. The system for operating a pharmacy in accordance with claim 26, wherein said data entry workstation comprises means for generating a code representative of a prescription number.

29. The system for operating a pharmacy in accordance with claim 26, further comprising a counseling workstation for providing information to a customer or to a pharmacist for purposes of counseling said customer.

30. The system for operating a pharmacy in accordance with claim 26, further comprising a point-of-sale (POS) workstation for providing a filled prescription to a customer and for receiving payment therefor.

31. The system for operating a pharmacy in accordance with claim 28, wherein said code comprises a barcode.

32. The system for operating a pharmacy in accordance with claim 27, further comprising means for preventing label printing until said prescription is ready to be filled at said filling workstation.

33. The system for operating a pharmacy in accordance with claim 26, further comprising a counseling workstation and a second printer for printing patient information.

34. The system for operating a pharmacy in accordance with claim 33, wherein said second printer is adapted to print auxiliary labels.

35. The system for operating a pharmacy in accordance with claim 26, wherein said data entry workstation is adapted to receive electronically transmitted prescriptions from physicians or from other pharmacies or from other sources holding prescriptions for at least one predetermined patient.

36. The system for operating a pharmacy in accordance with claim 26, further comprising an electrical switching device for switching peripheral equipment from said pharmacy management system computer to any of said workstations and from any of said workstations to said pharmacy management system computer.

37. The system for operating a pharmacy in accordance with claim 33, wherein any of said workstations comprises a software display window for emulating a terminal into said pharmacy management system.

38. The system for operating a pharmacy in accordance with claim 26, further comprising a point-of-sale terminal comprising a barcode reader for identifying prescriptions for which payment is to be made.

39. The system for operating a pharmacy in accordance with claim 38, wherein said point-of-sale terminal further comprises a signature pad for recording an image of the signature of a patient.

40. The system for operating a pharmacy in accordance with claim 27, wherein said means for introducing said prescription image comprises a digital camera.

41. The system for operating a pharmacy in accordance with claim 33, further comprising a display operatively connected to one of said workstations for displaying a list of prescriptions to be filled, said list of prescriptions being presented in the order in which said prescriptions are to be filled.

42. The system for operating a pharmacy in accordance with claim 41, wherein said order of said list of prescriptions may be modified by an operator.

43. The system for operating a pharmacy in accordance with claim 26, further comprising a database server for accepting database entries and changes thereto from any of said workstations, and for providing data thereto, upon request.

44. The system for operating a pharmacy in accordance with claim 26, in which a pharmacist may perform a drug utilization review, an adjudication with an insurance company or HMO, a formulary drug substitution, a price check, or other pharmacy management system function.

45. The system for operating a pharmacy in accordance with claim 26, further comprising means for accessing the Internet for tutorial material to be provided to a patient.

46. The system for operating a pharmacy in accordance with claim 26, further comprising means for screening the blood pressure of a patient and recording the results thereof in a database record for said patient.

47. The system for operating a pharmacy in accordance with claim 26, further comprising means for videoconferencing with third parties for obtaining information useful to a patient.

48. The system for operating a pharmacy in accordance with claim 27, further comprising means for allowing a patient to view said display to verify that a prescription, as dispensed, contains correct medication.

49. The system for operating a pharmacy in accordance with claim 27, wherein said display is also adapted to display recipes or instructions for compounding drugs or reconstituting drugs.

50. The system for operating a pharmacy in accordance with claim 33, wherein said counseling workstation further comprises a signature pad for recording an image of the signature of a patient.

51. The system for operating a pharmacy in accordance with claim 33, wherein any of said workstations stores a database of patient information, prescriptions and medication.

52. The system for operating a pharmacy in accordance with claim 33, further comprising a database server for storing a database of patient information, prescriptions and medication.

53. The system for operating a pharmacy in accordance with claim 26, further comprising a display on which said data and an image of said prescription appears.

54. The system for operating a pharmacy in accordance with claim 26, further comprising a display on which said data and an image of a drug type appears.

55. The system for operating a pharmacy in accordance with claim 26, further comprising means to allow any workstation to do the work of any other workstation.

56. The system for operating a pharmacy in accordance with claim 27, further comprising a display at the checking workstation displaying a clinical description in words of the drug called for in the prescription being checked.

57. The system for operating a pharmacy in accordance with claim 56, further comprising a display at the checking workstation displaying a clinical description in words, said clinical description comprising the size, type, shape, color, and markings of the medication being checked.

* * * * *